United States Patent
Bravo de Vega et al.

(10) Patent No.: US 9,931,839 B1
(45) Date of Patent: Apr. 3, 2018

(54) BEAM ANGLES OF DROP DETECTORS

(71) Applicant: HEWLETT-PACKARD DEVELOPMENT COMPANY, L.P., Houston, TX (US)

(72) Inventors: Jose Francisco Bravo de Vega, Sant Cugat del Valles (ES); Francisco Gomez, Sant Cugat del Valles (ES); Jordi Bas, Sant Cugat del Valles (ES); Alejandro Mielgo, San Cugat del Valles (ES)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 15/380,125

(22) Filed: Dec. 15, 2016

(51) Int. Cl.
  *B41J 2/045* (2006.01)
  *B41J 2/125* (2006.01)
  *G01N 21/55* (2014.01)
  *G01N 21/85* (2006.01)
  *G01N 21/47* (2006.01)
  *B41J 2/21* (2006.01)
  *B41J 2/165* (2006.01)

(52) U.S. Cl.
  CPC .......... *B41J 2/04561* (2013.01); *B41J 2/125* (2013.01); *B41J 2/16579* (2013.01); *B41J 2/2142* (2013.01); *G01N 21/47* (2013.01); *G01N 21/55* (2013.01); *G01N 21/85* (2013.01); *G01N 2201/0626* (2013.01)

(58) Field of Classification Search
  CPC .... B41J 2/04561; B41J 2/125; B41J 2/16579; B41J 2/21; B41J 2/2142; G01N 21/47; G01N 21/55; G01N 21/85
  See application file for complete search history.

(56) References Cited

U.S. PATENT DOCUMENTS 4,315,147 A    2/1982   Harmer et al.
4,754,289 A    6/1988   Kudo
(Continued)

FOREIGN PATENT DOCUMENTS

WO    WO-2014092678    6/2014

OTHER PUBLICATIONS

Trondle, J. et al, Non-contact Optical Sensor to Detect Free Flying Droplets in the Nanolitre Range. Feb. 11, 2010 <https://www.imtek.de/data/lehrstuahla/app/dokumente/publikationen/publpdf2010/troendle-non-contact-optical-sensor.pdf>.

(Continued)

*Primary Examiner* — Anh T. N. Vo
(74) *Attorney, Agent, or Firm* — HP Inc. Patent Department

(57) ABSTRACT

In some examples, a printhead drop detector comprises a plurality of drop detection units to detect any drops passing through a sampling volume between the radiation source and the radiation detector. A radiation detector of a first drop detection unit and a radiation source of a second drop detection unit is arranged on a first side of the sampling volume and a radiation source of the first drop detection unit and a radiation detector of the second drop detection unit is arranged on the second side of the sampling volume. The distance between the first drop detection unit and the second drop detection unit is based on an angle of a beam producible by the first radiation source such that the beam is wide enough to cross into a portion of the sampling volume corresponding with the second drop detection unit.

15 Claims, 2 Drawing Sheets

(56) References Cited

U.S. PATENT DOCUMENTS

| | | | |
|---|---|---|---|
| 5,350,929 A | 9/1994 | Meyer et al. | |
| 5,430,306 A | 7/1995 | Ix | |
| 6,350,006 B1 * | 2/2002 | Muller | B41J 29/393 347/19 |
| 6,513,900 B2 | 2/2003 | Endo et al. | |
| 6,648,444 B2 * | 11/2003 | Valero | B41J 2/16579 347/19 |
| 7,815,280 B2 * | 10/2010 | Hayashi | B41J 2/2142 347/19 |
| 8,419,159 B2 | 4/2013 | Govyadinov et al. | |
| 8,449,068 B2 | 5/2013 | Govyadinov et al. | |
| 8,529,011 B2 * | 9/2013 | Govyadinov | B41J 2/0456 347/19 |
| 9,056,465 B2 | 6/2015 | Massen | |
| 9,268,023 B2 | 2/2016 | Garay et al. | |
| 2004/0119779 A1 | 6/2004 | Elgee | |
| 2007/0024658 A1 | 2/2007 | Diol et al. | |
| 2013/0293625 A1 | 11/2013 | Massen | |
| 2014/0078213 A1 | 3/2014 | Govyadinov | |

OTHER PUBLICATIONS

International Searching Authority. ISA/EP. International Search Report. Application No. Ep/2015/065126, dated Mar. 29, 2016. 4 pages.

Thurow, K. et al., "An Optical Approach for the Determination of Droplet Volumes in Nanodispensing", Feb. 10, 2009. Journal of Automated Methods and Management in Chemistry, vol. 2009, Article ID 198732, 10 pages.

* cited by examiner

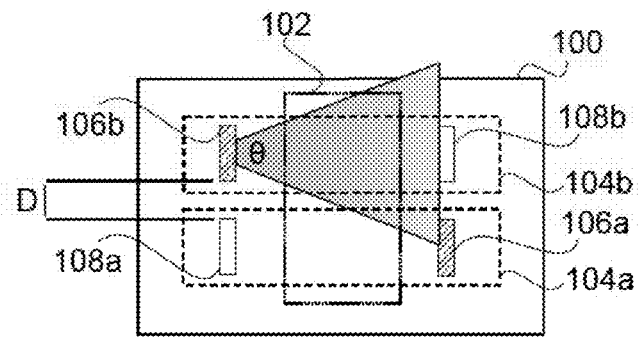
Fig. 1a
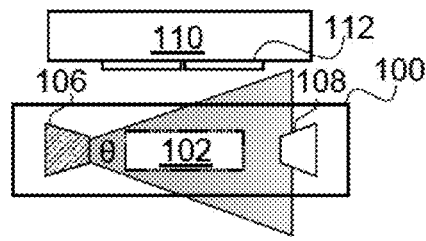
Fig. 1b
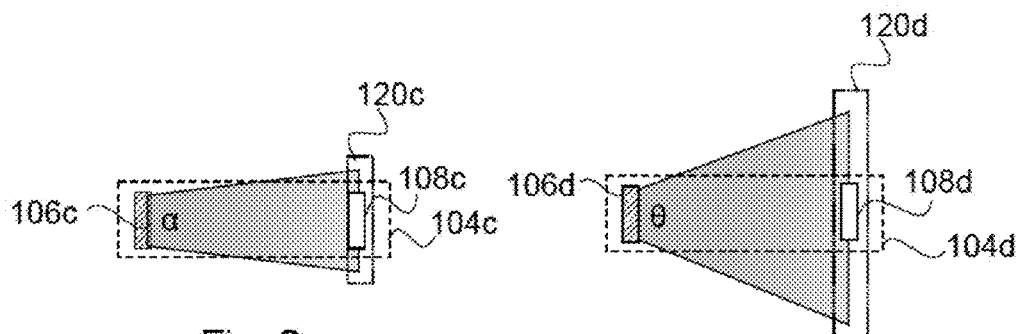
Fig. 2a
Fig. 2b
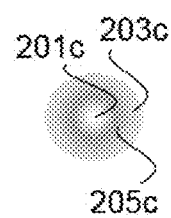
Fig. 2c
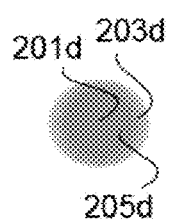
Fig. 2d

BEAM ANGLES OF DROP DETECTORS

BACKGROUND

Some print apparatus disperse print materials such as coloring agent, for example comprising a dye or colorant, from a printhead. An example printhead includes a set of nozzles and a mechanism for ejecting a selected agent as a fluid, for example a liquid, through a nozzle. In such examples, a drop detector may be used to detect whether drops are being ejected from individual nozzles of a printhead. For example, a drop detector may be used to determine whether any of the nozzles are clogged and would benefit from cleaning or having some other maintenance operation performed thereon.

BRIEF DESCRIPTION OF DRAWINGS

Examples will now be described with reference to the accompanying drawings, in which:

FIGS. 1a and 1b are block diagrams of an example of a drop detector;

FIGS. 2a, 2b, 2c, and 2d are block diagrams of example drop detection units;

DETAILED DESCRIPTION

Figure 3:
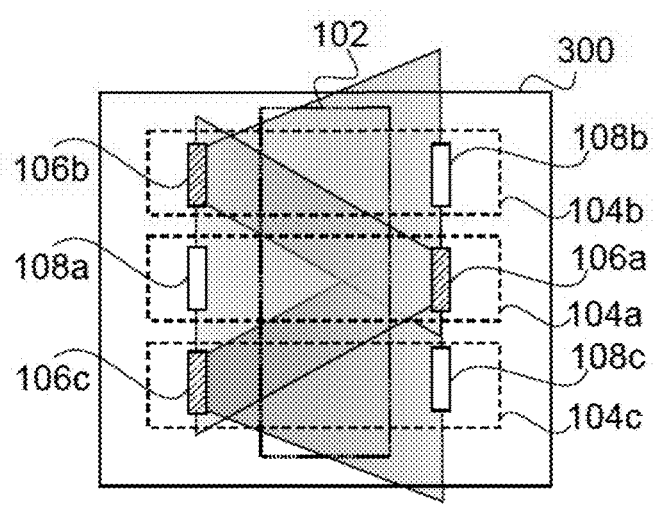
FIG. 3 is a block diagram of an example of a drop detector.

FIGS. 1a and 1b show, respectively, a top view and a side view of an example of a printhead drop detector 100. The printhead drop detector 100 comprises a plurality of drop detection units 104a, b. Each drop detection unit 104a, b comprises respective radiation sources 106a, b and respective radiation detectors 108a, b. The drop detection units 104 are to detect a drop of fluid (which may be, for example a print material such as an ink, coating or other print material) passing through a sampling volume 102 defined between the radiation source 106 and the radiation detector 108 of a unit 104. For example, if the radiation source 106 of a unit 102 is emitting optical radiation (i.e. light, which may in some examples be red light), the arrangement may be such that this light is incident on the radiation detector 108 of the unit 102. A drop passing therebetween creates a shadow and the intensity of light detected by the radiation detector 108 decreases, allowing the presence of a drop to be detected.

While the term 'drop detection unit' is used herein, this may not describe a separate or separable component, and instead may describe a functional pairing. The source 106 and radiation detector 108 of a drop detection unit 104 may therefore considered to be paired, forming an operative rather than structural unit.

As is shown in FIG. 1a, a radiation detector 108a of a first drop detection unit 104a and a radiation source 106b of a second drop detection unit 104b are arranged on the first side of the sampling volume 102. A radiation source 106a of the first drop detection unit 104a and a radiation detector 108b of the second drop detection unit 104b are arranged on the second side (which is opposed to the first side) of the sampling volume 102.

In some examples, the radiation sources 106 may comprise at least one light source, for example an LED (Light Emitting Diode), and/or the radiation detectors 108 may comprise at least one photodetector, for example a photodiode.

The drop detection units 104a, b are spaced apart by a distance D with a distance-to-angle relationship where the angle $\theta$ of the beam of the LED (106b) of a second drop detection unit 104b is wide enough to cross into a portion of the sampling volume 102 corresponding with the second drop detection unit 104a.

FIG. 1b shows an example printhead 110 having a print surface 112 which includes nozzles to deposit print fluid across the sampling volume 102. The angle $\theta$ of the beam from the radiation source 106 is less than that which causes reflections from the printing surface 112 of the printhead 110. For example, if the angle of the beam is such that the beam reaches the surface 112 of the printhead (e.g., the side of the print head that deposits ink, such as the printhead dies), the surface of the printhead (e.g., depending on the contours and/or materials, etc.) may reflect any light that falls on the surface, which may reflect towards the radiation detectors 108. Thus, the limit of the angle used by the drop detection units 104 may be based on the distance between the drop detector 100 and the printhead 110 as implemented in a particular printer model. This may avoid false detections or other errors associated with operation of the drop detector 100.

FIGS. 2a, 2b, 2c, and 2d are block diagrams of example drop detection units 104c, 104d. FIG. 2a shows an example of a drop detection unit 104c where the beam produced from radiation source 106c has an angle $\alpha$ such that the radiation does not cross into sampling volumes beyond that corresponding to the drop detection unit 104c. In other words, the annular beam may have a width 120c at the second side of the drop detector and may encompass the radiation detector 108 without extending to encompass the components of other drop detection units.

FIG. 2b shows an example where the drop detection unit 104d includes a radiation source 106d that produces a beam at an angle $\theta$ where $\theta$ is greater than $\alpha$. For example, the annular beam may have a width 120d at the second side of the drop detector and may encompass the radiation detector 108d as well as extending to encompass the components of other drop detection units, such as a radiation source of an adjacent drop detection unit. The directed annular beam produced by the radiation source 106d may have an angle $\theta$ between about 6 degrees and about 12 degrees. Other example ranges of beam angles that may be usable with the drop detectors described herein include a beam angle greater than 6 degrees and less than 10 degrees and a beam angle that is greater than about 7 degrees and less than about 9 degrees.

FIG. 2c shows an example representation of a section of the beam produced by a radiation source 106c of a drop detection unit 104c at a side of a drop detector where the corresponding radiation detector 108c is located. The intensity at a portion of the beam may be measured by relative luminous intensity, which is a level of intensity relative to the maximum luminosity of the radiation source. For example, the relative luminous intensity approaches 1 as current through an LED increases and approaches 0 as the current through the LED decreases. A directed beam with such an angle $\alpha$ may generate a non-uniform intensity range of radiation. An example may be a ring phenomenon, where the intensity of light near the edge of the beam is substantially greater than the intensity of light near the center of the beam. For example in FIG. 2c, the radiation intensity level at 201c may have a relative luminous intensity of 0.4 while the radiation intensity levels at 203c and 205c may have a relative luminous intensity of 0.3 and 0.8, respectively.

FIG. 2d shows an example representation of a section of the beam produced by a radiation source 106d of a drop detection unit 104d at a side of a drop detector where the corresponding radiation detector 108d is located. An annular beam with such an angle of θ may generate a substantially uniform intensity range of radiation. For example in FIG. 2d, the radiation intensity level at 201d may have a relative luminous intensity of 0.6] while the radiation intensity levels at 203d and 205d may have a relative luminous intensity of 0.7 and 0.8, respectively. In this manner, the beam produced by the radiation source 106d is wider than the beam produced by radiation source 106c to generate a beam with a greater uniformity of radiation intensity across the beam with comparison to the beam of radiation source 106c, where the greater beam uniformity allows for improved accuracy of radiation detection by the radiation detector 108d, for example.

The radiation source 106d, such as an LED, may selected for use with the drop detector such that the intensity range of the beam of the LED may be below a threshold distribution at the radiation detector or above a threshold intensity level, such as within about 20% of the median intensity level. For another example, the central area of the light beam (i.e., the area of the beam within a one degree angle from the center) projected from an LED is a relative luminous intensity of 0.5 for a distance at least equal or above the distance from the LED to a photodiode on the opposing side of the drop detector. The threshold level may be associated with a level of luminous intensity, a degree of accuracy of detection, false positive level, vibration tolerance, or other quality of service factor.

FIG. 3 shows another example of a printhead drop detector 300. This example is similar to the example of FIG. 1 (and like parts are labelled with like numbers) but comprises an additional drop detection unit 104c comprising a radiation source 106c and a radiation detector 108c.

As is shown in FIG. 3, the radiation detector 108a of a first drop detection unit 104a and the radiation source 106b, c of the second and third drop detection unit 104b, c are arranged on the first side of the sampling volume 102; and the radiation source 106a of the first drop detection unit 104a and the radiation detector 108b, c of the second and third drop detection unitsl04b, c are arranged on the second side of the sampling volume 102. The first drop detection unit 104a is arranged between the second 104b and third 104c drop detection units.

In the examples of FIGS. 1 and 3, radiation detectors 108 and radiation sources 106 on each side of the sampling volume 102 are arranged such that no radiation detector 108 is adjacent to another radiation detector 108, and a radiation source 106 is not adjacent to another radiation source 106. In other words, the arrangement comprises, on opposed sides of the sampling volume 102, alternating radiation detectors 108 and radiation sources 106. The arrangement is such that there is a first row of alternating radiation sources 106, or emitters, and radiation detectors 108 or receiver and second row of alternating radiation emitters/sources and detectors/receivers. Each emitter 106 of the first row is to emit radiation to be received by an associated radiation detector 108 (in the example of FIG. 1, the detector of the same drop detection unit 104) of the second row, and each emitter 106 of the second row is to emit radiation to be received by an associated radiation detector 108 of the first row.

Light, when emitted from a source or an aperture, tends to spread in an effect termed dispersion. While dispersion is less apparent for certain highly directional radiation sources, such as lasers, these tend to be expensive. The light from one source 106 may be incident not just on the associated radiation detector 108, but also on a region around that radiation detector 108. Therefore, care should be taken in designing a drop detector such that the light from sources of other units 104 incident on a radiation detector of a particular unit is not of a sufficient level that it could cause a false negative. A 'false negative' result is seen when the intensity of light at a radiation detector leads to a conclusion that there is no drop when in fact a drop has been ejected: if light of sufficient intensity is received, a drop may be assumed to be absent, even when that light is received from the radiation source of another unit.

If, for example, in an alternative arrangement to that shown in FIGS. 1 and 3, the radiation detectors are all arranged on one side of the sampling volume and the sources on another, design of a drop detector may be such that the separation of radiation detectors is sufficient to ensure that light from sources of other units incident on a radiation detector of a particular unit is not of a sufficient level that it could cause a false negative. Such separation means that the arrangement of detectors is not compact.

In the examples of FIGS. 1 and 3, however, because the radiation detectors 108 and sources 106 are arranged alternately, the units 104 may be closely packed without the need for any additional light blocking measures, and the risk of 'false negatives' due to the effects described above is reduced or removed. Each radiation source 106 which separates any two radiation detectors 108 provides detector separation while allowing the footprint of an array of a particular number of drop detection units 104 to be reduced. However, the drop detection units 104 may be implemented to overlap or otherwise cross into the sampling volume corresponding to other detection units. This may allow for the radiation sources 106 to produce a substantially uniform beam to improve accuracy of radiation detection by the radiation detectors 108 while the overlap of the beams may have insignificant effect has it is restricted to overlap between emitters106 of adjacent detection units 104 and not the detectors 108. In other words, arranging the units 104 with alternating orientations reduces any disadvantageous effects of interference from neighboring units 104 as long as the beams produced by the radiation sources 106 do not cross a sampling volume that includes multiple radiation detectors 108.

The drop detector 300 may include a first row and second row of alternating radiation emitters and radiation detectors to be used with a printhead to detect drops ejected from the printhead. For example, each further emitter of the first row is to emit radiation to be received by a paired radiation detector of the second row, each emitter of the second row is to emit radiation to be received by a paired radiation detector of the first row, and each emitter of the first row and the second row is to emit radiation at an angle based on alternating positions of the radiation detectors where the angle of radiation of each emitter is sufficient to encompass emitters adjacent the paired radiation detector corresponding to the particular emitter. The radiation produced by the radiation emitters may cross the sections of sampling volume of the corresponding drop detection units, but may also cross to the sections of sampling volume corresponding to other drop detection units. Thus, an overlap of beams may occur, such as shown in FIG. 3. For example, the radiation source of the first drop detection unit produces a beam with an angle that encompasses the radiation source of the second drop detection unit adjacent to the radiation detector of the first drop detection unit. In other examples, the radiation source of the first drop detection unit produces a beam with an angle equivalent to an angle of a beam of the radiation source of the second drop detection unit, the angle of the beam of the radiation source of the first drop detection unit to avoid capture of the radiation detector of a third drop detection unit adjacent the second drop detection unit. A drop detector 300 with alternating drop detection units 104 is able to have wider beams than drop detection units with all the radiation sources 106 all on a single side of the drop detector (e.g., allows the beam to overlap on the nearby LEDs without substantial disadvantageous effect on the photodiodes), for example, even to be able to use a beam that is wide enough to achieve a uniformity threshold of radiation intensity to improve detection accuracy at the radiation detectors 108.

The limits of the beam angle may correspond to the limits of the area of the drop detector and the number of drop detection units (and location of the drop detection units). For example, a drop detector unit to detect a drop passing through a sampling volume between the emitter and the receiver may have the units arranged such that, on opposed sides of the sampling volume, emitters and receivers are provided alternately, wherein the emitters provide a beam with an angle that is greater than that which causes an intensity range of radiation above a threshold distribution at the receivers; and less than that which causes reflections from the printing surface of the printhead.

Figure 4:
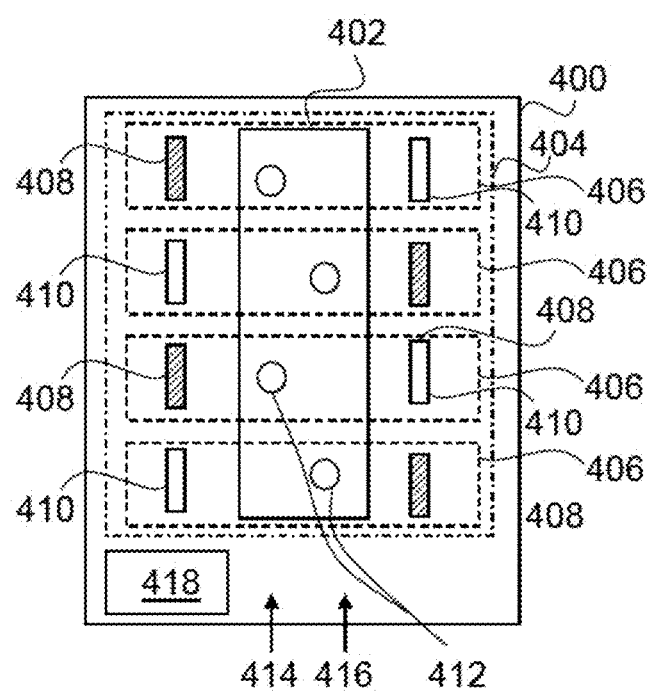
FIG. 4 is a block diagram of an example of a print apparatus comprising a drop detector.

FIG. 4 shows an example of a print apparatus 400 comprising a printhead 402 and a drop detector 404. The printhead 402 is to selectively deliver a print material; and the drop detector 404 is to monitor the ejection of print material from the printhead 402. In one example, the printhead 402 uses inkjet technology to eject print material therefrom. The drop detector 404 comprises a plurality of drop detection units 406, each drop detection unit 406 comprising an emitter 408 (for example, a radiation source) and a receiver 410 (for example a radiation detector). The units 406 are to detect a drop passing through a sampling volume (not marked) between an emitter 408 and a receiver 410, and are arranged such that, on each side of the sampling volume, emitters 408 and receivers 410 are provided alternately. In examples, the drop detector 400 may be a drop detector 100, 300 as described in relation to FIG. 1 or 3.

The printhead 402 comprises a plurality of nozzles 412, the nozzles being arranged in a first column 414 and a second column 416, spaced from the first column 414, wherein the nozzles 412 of the first column 414 are at least substantially parallel to and offset from the nozzles 412 of the second column 416 (i.e. the nozzles 412 are staggered such that, in a first dimension, the nozzles 412 of the first column 414 are interspersed with the nozzles of a second column 416). The columns 414, 416 are also at least substantially parallel to the rows of alternating radiation emitters 408 and receivers 410 arranged on each side of the sampling volume.

Such a distribution of nozzles 412 may be employed in order to improve the smoothness of a printed output. Each unit 406 is associated with one nozzle 412, and may detect the emission (or in some examples, the absence) of a drop from that associated nozzle 412.

It will be noted that each nozzle 412 which is associated with a particular unit 406 is selected from the column 414, 416 which is closer than the other column 414, 416 to the emitter 408. Indeed, in this example, the nozzles 412 are arranged so as to be closer to the emitter 408 of the associated unit 406 than to the receiver 410 of that unit 406.

Due to the effects of dispersion, the cross sectional surface area of a light beam, or a beam of other radiation, leaving the emitter 408 increases with distance from the emitter 408. For some drops, therefore, it may be the case that the drop spans the whole of a beam when the drop falls relatively close to the emitter 408 (i.e. the cross-sectional area of the beam at that point may be smaller than, or comparable to, the size of the drop). However, as the distance from the emitter 408 increases, the whole beam may not be obscured. This means that some light may still reach the receiver 410. Even in examples where the reduction in intensity may be sufficient to determine if a drop is present or not, there may be a reduction in the variability of the intensity detected, and therefore the detection task is harder, more error prone and/or may be implemented by more sensitive detection apparatus.

Moreover, in the manufacture of some LEDs and other light emitters, an excitation pad is arranged in the center of the emitter. This can create a "dark spot" in the center of an emitted beam, which may in some examples become large in the far field. In some examples, such an arrangement of the excitation pad may be provided in an LED which is less directional (and/or less expensive).

The resulting beam for such light sources becomes annular in nature. In some drop detectors, a source and emitter may be separated across a sampling volume by a distance on the order of 30-60 mm. A drop breaking an emitted beam at a distance of around 10-25 mm may substantially block the beam. However, a drop passing through the beam at around 30-60 mm may pass through an upper region of the annulus of light, a region of the dark spot and then through the lower region of the annulus. As a result, a detector signal for a relatively distant drop will show a 'double peak', where the drop breaks the annulus, but the overall signal will be smaller than for a relatively closer drop.

The alternating configuration of drop detection units in the example of FIG. 4 corresponds with the staggered arrangement of nozzles 412, and means that the drops tend to fall through the sampling volume at a distance which is relatively close to the emitter 408. Therefore, compared to an arrangement where the radiation detectors are on one side of the sampling volume, and the emitters on the other side, in which case the drops from one column 414, 416 would fall relatively close to the emitters, and the drops of the other column 414, 416 would fall relatively far from the emitters, all of the units 406 in the example of FIG. 4 are arranged such that a drop will fall relatively close to the emitter 408. In this manner, the drop detector 404 may be arranged below the printhead to coordinate positions of the nozzles 412 to coordinate the column of the location of the nozzle 412 is closer to the corresponding emitter 408 than the corresponding receiver 410. The angle and/or width of the beam of the emitter 408 may be set with respect to the nozzles to limit the number of drops from different nozzles. For example, a beam of a radiation detector 408 on a first side of the drop detector 404 may be wide enough to intersect drops from one nozzle of column 414 and two drops from column 416 and a beam of a radiation detector 408 on a second side of the drop detector 404 may be wide enough to intersect drops from one nozzle of column 416 and two drops from column 414.

The print apparatus 400 in this example further comprises a processor 418 to receive data from the receiver 410 and to determine a performance indication for the printhead 402, for example whether print material has been ejected from a selected nozzle 412.

In this example, the processor 418 receives data gathered by the drop detector 404 and uses this data to determine if agent is actually ejected from a selected nozzle 412 as intended, and thereby can determine a performance indication for the printhead 402.

In some examples, a drop detector 404 may be moveably mounted so that it can be repositioned to monitor different nozzles 412.

Although in the illustrated example, four units 406 are shown, there may be more or fewer units 406. In one example, there are twelve units 406.

In some examples, the print apparatus 400 may comprise additional components, such as motors, fluid ejection mechanisms and the like.

In the example above, light intensity is detected. Other examples may use other technologies such as detecting changes in refractive index, inductive electrification, humidification and the like.

The term 'processor' is to be interpreted broadly to include a CPU, processing unit, ASIC, logic unit, or programmable gate array etc. The methods and functional modules may all be performed by a single processor or divided amongst several processors.

While the apparatus and related aspects have been described with reference to certain examples, various modifications, changes, omissions, and substitutions can be made without departing from the spirit of the present disclosure. It should be noted that the above-mentioned examples illustrate rather than limit what is described herein, and that those skilled in the art will be able to design many alternative implementations without departing from the scope of the appended claims.

The word "comprising" does not exclude the presence of elements other than those listed in a claim, "a" or "an" does not exclude a plurality, and a single processor or other unit may fulfil the functions of several units recited in the claims. The use of "first," "second," etc. are not meant to designate an order or other limiting effect, but are used to identify a particular element from another.

Features discussed in relation to one example may replace, or be replaced by, features from another example.

The features of any dependent claim may be combined with the features of any of the independent claims or other dependent claims.

The invention claimed is:

1. A printhead drop detector comprising:
   a plurality of drop detection units, each drop detection unit comprising a radiation source and a radiation detector to detect a drop passing through a sampling volume between the radiation source and the radiation detector, wherein
   a radiation detector of a first drop detection unit and a radiation source of a second drop detection unit are arranged on a first side of the sampling volume; and
   a radiation source of the first drop detection unit and a radiation detector of the second drop detection unit are arranged on a second side of the sampling volume; and
   a distance between the first drop detection unit and the second drop detection unit is based on an angle of a beam producible by the first radiation source such that the beam is wide enough to cross into a portion of the sampling volume corresponding with the second drop detection unit.

2. The printhead drop detector of claim 1, wherein the radiation source produces a beam having an intensity range below a threshold distribution at the radiation detector.

3. The printhead drop detector of claim 1, wherein the radiation source produces a beam angle between about 6 degrees and about 12 degrees.

4. The printhead drop detector of claim 1, wherein the radiation detectors and radiation sources on each side of the sampling volume are light emitting diodes and photodiodes arranged in a linear manner, the arrangement on each side of the sampling volume comprising alternating light emitting diodes and photodiodes.

5. The printhead drop detector of claim 1, wherein the radiation source of the first drop detection unit produces a beam with an angle equivalent to an angle of a beam of the radiation source of the second drop detection unit, the angle of the beam of the radiation source of the first drop detection unit to avoid capture of the radiation detector of a third drop detection unit adjacent the second drop detection unit.

6. The printhead drop detector of claim 1, wherein the radiation source of the first drop detection unit produces a beam with an angle that encompasses the radiation source of the second drop detection unit adjacent to the radiation detector of the first drop detection unit.

7. A print apparatus comprising:
   a printhead to selectively eject a print material from a printing surface; and
   a drop detector to monitor the ejection of print material from the printhead, the drop detector comprising a plurality of drop detection units, each drop detection unit comprising an emitter and a receiver to detect a drop passing through a sampling volume between the emitter and the receiver, wherein the units are arranged such that, on opposed sides of the sampling volume, emitters and receivers are provided alternately, wherein the emitters provide a beam with an angle that is:
   greater than that which causes an intensity range of radiation above a threshold distribution at the receivers; and
   less than that which causes reflections from the printing surface of the printhead.

8. The print apparatus of claim 7, wherein the printhead comprises a plurality of nozzles, the nozzles being arranged in a first column and a second column, spaced from the first column, wherein the nozzles of the first column are parallel to and offset from the nozzles of the second column.

9. The print apparatus of claim 8, wherein each nozzle is associated with a drop detection unit, an associated nozzle being in the column which is relatively closer to the emitter of the drop detection unit associated therewith than the other column.

10. The print apparatus of claim 8, wherein each nozzle is associated with a drop detection unit, an associated nozzle being positioned relatively closer to the emitter than to the receiver of the drop detection unit.

11. The print apparatus of claim 7, wherein the angle of the beam is greater than 6 degrees and less than 10 degrees.

12. The print apparatus of claim 7, wherein the angle of the beam is greater than about 7 degrees and less than about 9 degrees.

13. The print apparatus of claim 7, further comprising a processor to receive data from the detector and to determine a performance indication for the printhead, wherein the printhead comprises a set of nozzles, and the processor is to determine if agent is ejected from a selected nozzle.

14. The print apparatus of claim 7, wherein the printhead comprises a plurality of columns of nozzles to eject printing agent, wherein each paired radiation emitter and radiation detector is to detect printing agent ejected from a nozzle associated with that paired radiation emitter and radiation detector, wherein in use of the drop detector with the printhead, a nozzle associated with a paired radiation emitter and radiation detector is within the columns of nozzles which is closer to the associated emitter, in which the rows of alternating radiation emitters and radiation detectors are parallel to one another and for use with the printhead having columns of nozzles which are, in use of the drop detector with the printhead, arranged parallel to the rows of alternating radiation emitters and radiation detectors.

15. A drop detector for use with a printhead, the drop detector comprising:
  a first row and second row of alternating radiation emitters and radiation detectors,
  wherein:
    each further emitter of the first row is to emit radiation to be received by a paired radiation detector of the second row,
    each emitter of the second row is to emit radiation to be received by a paired radiation detector of the first row, and
    each emitter of the first row and the second row is to emit radiation at an angle based on alternating positions of the radiation detectors, the angle of radiation of each emitter to encompass emitters adjacent the paired radiation detector corresponding to the particular emitter.

* * * * *

UNITED STATES PATENT AND TRADEMARK OFFICE
CERTIFICATE OF CORRECTION

PATENT NO. : 9,931,839 B1
APPLICATION NO. : 15/380125
DATED : April 3, 2018
INVENTOR(S) : Jose Francisco Bravo de Vega et al.

It is certified that error appears in the above-identified patent and that said Letters Patent is hereby corrected as shown below:

On the Title Page

Item (72), Inventors, in Column 1, Line 5, delete "San Cugat del Valles, ES" and insert -- Sant Cugat del Valles, ES --, therefor.

Signed and Sealed this
Twentieth Day of November, 2018

Andrei Iancu
*Director of the United States Patent and Trademark Office*